United States Patent [19]

Alcala

[11] Patent Number: 5,315,993
[45] Date of Patent: May 31, 1994

[54] LUMINESCENCE MONITORING WITH MODULATION FREQUENCY MULTIPLEXING

[75] Inventor: J. Ricardo Alcala, Chatham, N.J.

[73] Assignee: The Boc Group, Inc., New Providence, N.J.

[21] Appl. No.: 827,658

[22] Filed: Jan. 29, 1992

Related U.S. Application Data

[63] Continuation-in-part of Ser. No. 481,406, Feb. 16, 1990, Pat. No. 5,151,869, and a continuation-in-part of Ser. No. 481,131, Feb. 16, 1990, Pat. No. 5,127,405.

[51] Int. Cl.$^5$ .......................... A61B 5/00; G01N 21/61
[52] U.S. Cl. .................................. 128/634; 422/82.06; 422/82.07; 250/458.1; 250/461.2
[58] Field of Search .............................. 128/633–635, 128/664–665; 422/82.06–82.07, 52, 86; 250/227.21, 458.1, 461.1–461.2; 385/123

[56] References Cited

U.S. PATENT DOCUMENTS

| | | | |
|---|---|---|---|
| 5,000,901 | 3/1991 | Iyer et al. | 128/634 X |
| 5,102,625 | 4/1992 | Hilo | 128/634 X |
| 5,119,463 | 6/1992 | Vurek et al. | 128/634 X |
| 5,127,405 | 7/1992 | Alcala et al. | 128/634 X |

FOREIGN PATENT DOCUMENTS

| | | |
|---|---|---|
| 0442276A1 | 8/1991 | European Pat. Off. . |
| WO9009637 | 8/1990 | PCT Int'l Appl. . |

OTHER PUBLICATIONS

"Rapid-Scanning Frequency-Domain Fluorometer With Picosecond Time Resolution," Applied Optics, vol. 26, No. 17, Sep. 1987.

"2-GHz Frequency-Domain Fluorometer," Rev. Sci. Instrum. 57(10) Oct. 1986, American Institute of Physics (1986).

"Digital Parallel Acquisition in Frequency Domain Fluorimetry", Rev. Sci. Instrum. 60(9), Sep. 1989, American Institute of Physics (1989).

*Primary Examiner*—Angela D. Sykes
*Attorney, Agent, or Firm*—Roger M. Rathbun; Larry R. Cassett

[57] ABSTRACT

A luminescence based analytical probe is excited with light varying repetitively in amplitude at multiple modulation frequencies. A composite signal incorporating components at a plurality of these modulation frequencies, produced by emissions in all of the various decaying modes is analyzed to provide information, such as the fractional luminescence contribution and/or lifetime of each individual decaying mode because the various decaying mode are segregated by analysis of the composite signal, there is no need to segregate light from the various decaying mode according to the wavelength of the light. Therefore, the probe may incorporate plural luminescent materials which have different decay modes with different luminescent decay times and sensitive to different conditions to be monitored, even if the plural luminescent materials absorb and emit light at the same wavelengths.

21 Claims, 3 Drawing Sheets

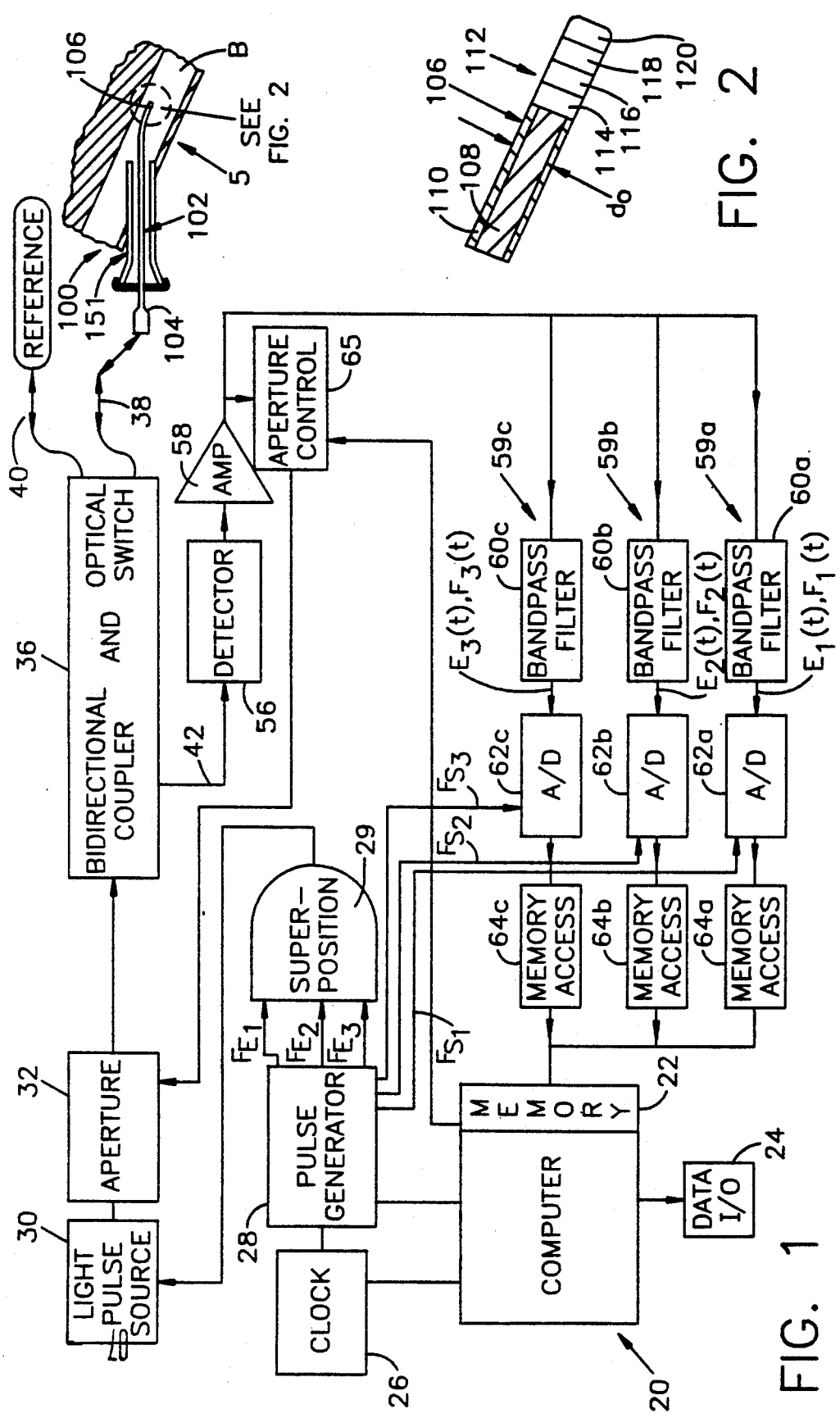

LUMINESCENCE MONITORING WITH MODULATION FREQUENCY MULTIPLEXING

CROSS REFERENCE TO RELATED APPLICATIONS

The present application is a continuation-in-part of copending, commonly, assigned U.S. Pat. Nos. 5,151,869 and 5,127,405 both filed Feb. 16, 1990. The disclosure of said applications is hereby incorporated by reference herein.

BACKGROUND OF THE INVENTION

It has long been recognized that the fluorescent and phosphorescent properties of certain materials vary in accordance with properties of the surroundings. For example, certain luminescent materials are subject to "quenching" or extinction of their luminescent response by oxygen. Quenching reduces the lifetime of the luminescence,, and also reduces the intensity of the luminescence. Other luminescent materials can be quenched by other chemical substances. Still others have luminescent properties which vary with temperature. In laboratory experiments where substantial amounts of luminescent materials can be directly illuminated and observed under readily controlled conditions, either the total luminescent intensity or the lifetime of the luminescence can be observed.

Chemical compositions of interest may have decay times ranging from seconds to picoseconds. With very short-lived luminescence, it is normally not practical to obtain useful information simply by exposing the composition to light, terminating the exposure and observing the decay of luminescence directly.

However, it is possible to obtain equivalent information by exposing the composition to excitation light having amplitude varying at a predetermined excitation modulation frequency and observing the luminescent response of the composition. Typically, the response includes a component varying in intensity at the same frequency as the excitation light. One characteristic of the emitted light which can be observed is the degree of modulation at the particular frequency used, i.e., the ratio between the intensity of the component at this frequency and the total intensity of the emitted light. Another characteristic of the emitted light which can be observed is the phase relationship between the cyclic variations in the emitted light and the cyclic variations in the excitation light. It has been the practice heretofore to conduct experiments of this nature at numerous modulation frequencies and gather information such as degree of modulation, phase angle and the like at each such frequency. Depending on the lifetime of the decay being studied, the modulation frequencies may be in the Hertz to gigahertz range. Utilizing known techniques, significant information concerning the physical and chemical characteristics of the composition can be deduced from the information gathered using plural frequencies. These techniques are commonly referred to as "frequency-domain fluorometry" and "frequency-domain phosphorimetry".

In laboratory experiments, such frequency domain techniques can distinguish between plural, simultaneously-occuring decays having different lifetimes. Thus, Bright et al, Rapid-Scanning Frequency Domain Fluorometer with Picosecond Time Resolution, Applied Optics, Vol. 26 Number 17,pp. 3526-3529, notes that a frequency domain fluorometer can resolve the three different decay times of three different reagents in admixture with one another. Lakowicz et al, A 2GHz Frequency-domain Fluorometer . . . , SPIE Vol 743, Fluorescence Detection (1987, pp 2-8) notes that a frequency domain fluorometer can resolve plural decay times associated with plural modes of decay of a single substance.

In frequency domain phosphorimetry and fluorometry, the various excitation modulation frequencies normally have been applied in sequence, one frequency at a time. Substantial time is required to collect data for all of the various frequencies. This approach is unsuitable for application in dynamic systems where the composition is changing with time. Accordingly, there have been attempts made to obtain similar information by applying light at various frequencies simultaneously and then measuring the response at all of these various frequencies simultaneously.

Mitchell et al, U.S. Pat. No. 4,939,457 discloses a laboratory instrument in which the excitation light is applied as series of pulses at a fundamental pulse-repetition frequency. This pulsatile excitation light includes components amplitude-modulated at the fundamental frequency and at harmonics or integral multiples of that frequency. The response or emitted light likewise includes components modulated at all of these frequencies. Pulsatile mixing signal having a fundamental frequency and harmonic frequencies slightly different from the corresponding frequencies in the excitation signal is also generated. The gain of the detector used to convert the response light into electrical signals is varied in accordance with the mixing signal, thereby mixing the response light signal with the mixing signal. The resulting cross-correlated or mixed signal has a fundamental frequency equal to the difference between the fundamental modulation frequency of the response light and the fundamental frequency of the mixing signals, and has harmonics at frequencies equal to the differences between corresponding harmonics of the response and mixing signals. In theory, the cross-correlated signal is a replica of response light, but with low modulation frequencies such that the cross-correlated signal can be digitized by conventional digital sampling devices. These digital samples of the cross-correlated signal versus time are then converted via Fourier transformation to a frequency-domain representation, including phase and modulation values for the various frequencies. This approach, however, encounters substantial degradation of signal strength at the higher harmonics, and hence is useful only with relatively strong emitted light signals.

Various instruments have been proposed to exploit luminescent phenomena in chemical and/or physical measuring instruments. For example, U.S. Pat. No. 4,810,655 discloses an instrument for determining oxygen concentration by applying excitation light to a fluorescent material and observing the time dependence of fluorescence decay, as by determining a ratio of luminescence intensity between two different periods of time after excitation. As the oxygen concentration in the environment surrounding the luminescent material changes, the pattern of fluorescent decay with time also changes. The '655 instrument employs a "light pipe" for transmitting the requisite excitation light to the luminescent material and for transmitting the light back to a sensor. European Patent Application 0,283,289 monitors the intensity of long lived phosphorescent emissions from a phosphorescent material bonded to an end of an optical fiber. The optical fiber is small enough that it can be inserted through a small tube, such as an intravenous catheter or the like, so that the phosphorescent material lies within a blood vessel and acts as an in vivo $PO_2$ sensor. Other fiber optic based $PP_2$ sensors are disclosed in U.S. Pat. No. 4,476,870 and European Patent Application 0,252,578.

Sensing of multiple phenomena with a single probe has also been suggested. Thus Kane, U.S. Pat. No. 4,758,814 describes a pH and $PO_2$ sensor utilizing two fluorescent dyes which emit at different wavelengths. The emissions from one dye are affected by pH, whereas the emissions from another dye are affected by $O_2$. Thus the emitted light at one wavelength provides a measure of pH, whereas the emitted light at another wavelength provides a measure of $O_2$ concentration. Optical filtering is employed to segregate the response light from the two dyes so that their respective responses can be monitored separately.

Cubbers et al, U.S. Reissue Pat. No. 31,879 mentions the possibility of a composite luminescent element or "optode" having plural indicating substances embedded therein, again with signal segregation by light wavelength. Kelsius, Inc., PCT published application W088/05533 is directed generally to a sensor having a plurality of detectors incorporated therein.

These and other arrangements which rely on segregation by wavelength necessarily requires that the luminescent materials be selected to operate at different wavelengths. This restricts the choice of luminescent materials. Additionally, the required wavelength-restrictive optical filters may attenuate the desired wavelengths to some degreee, thus degrading the signal.

Although these and other fiber optic based luminescence probes and instruments have been proposed for monitoring chemical and/or physical conditions within the bodies of living subjects, the instruments available heretofore have suffered from certain significant drawbacks. For ease of insertion into the body through a needle or intravascular catheter, a fiber optic probe should be less than about 450 micrometers in diameter. The amount of luminescent material which can be accommodated in a probe of such small diameter is limited. The excitation light intensity must be maintained at a reasonable level to avoid destruction of the luminescent materials. For a given intensity level, the total excitation light energy which can be transmitted along the fiber optic is directly proportional to the cross-sectional area of the fiber optic. Thus, only limited light energy can be applied to excite the luminescent material. All of these factors tend to limit the amplitude of the response light emitted by the luminescent material and transmitted back along the fiber to the proximal end. Even highly sensitive photodetectors will provide only a weak signal. The signal from the actual luminescent material at the probe may be effectively hidden by the background noise. Stated another way, such instruments have had poor signal to noise ratios. This problem has been particularly severe in the case of instruments arranged to monitor the decay rate of relatively shortlived luminescent phenomena such as fluorescence or rapidly-decaying phosphorescence.

The frequency domain approach has not been generally applied in luminescence-based fiber optic sensing instruments. Instruments using one modulation frequency at a time acquire the necessary data too slowly for practical in vivo sensing. The signal attenuation encountered with the multiple harmonic cross-correlation approach normally renders this approach impractical for use with fiber optic systems.

The aforementioned U.S. Patent Application 07/481,406 discloses a substantial advance in frequency domain techniques. Instruments according to that application preferably include means for applying excitation light such as a series of pulses incorporating a plurality of excitation modulation frequency so that the luminescent material emits response light varying in amplitude at the same plural modulation frequencies. The excitation light typically is applied as a series of pulses at a fundamental with pulse frequency, so that the excitation light, and intensity response light emitted by the luminescent material include components varying at the fundamental and at harmonics of that frequency. One aspect of that disclosure involves the uses of direct sampling and, preferably, digitization, of the response light. For example, the response light may be converted to an electrical signal by a photodetector such that the instantaneous electrical signal from the photodetector is directly related to the instantaneous intensity or amplitude of the response light, and that signal may be directly sampled. The sampled response signal desirably is converted to a frequency domain representation of the response light, incorporating values of the modulation ratio and phase at each frequency. Preferably, a reference or excitation signal representing the excitation light is sampled, digitized and converted in substantially the same way so that the characteristics of each frequency in the response signal can be compared with the corresponding characteristics of the excitation light. For example, the phase of the response component at a particular modulation frequency can be compared directly with the phase of the excitation component at the same frequency. Preferred apparatus and methods according to the '406 application utilize sampling frequencies lower than the modulation frequencies. Various samples taken on different repetitions of the response and sample waveforms occur at different points along these waveforms and hence provide a complete sampling of the repetitive waveforms, in much the same way as if the sampling device operated at a much higher frequency. This arrangement permits effective sampling of very high frequency components, in the megahertz and gigahertz ranges using practical sampling devices. Because the response waveform (and reference waveform, where employed) are sampled directly without the need for mixing or cross-correlation prior to sampling, the signal loss in the higher harmonics associated with cross-correlation is effectively eliminated.

As described in greater detail in the aforementioned '131 application, such direct sampling and conversion techniques make it practical to apply frequency domain techniques to instruments using a fiber optic or similar light transmissive member and, particularly, a relatively small fiber optic probe as may be employed in monitoring chemical conditions within the body of a living subject. In particular, instruments using the technique of sampling and converting the response light signal to a frequency domain representation can be used with fiber optic probes insertable through an intravascular catheter insertable into the body of the subject through an intravascular catheter or similar device. Such instruments may employ luminescent materials having very fast decay times, and can detect very small changes in the decay times. This provides numerous benefits and generally superior performance to that achievable with other systems such as monitoring of emission intensity.

SUMMARY OF THE INVENTION

The present invention provides further improvements in probes, apparatus and methods for monitoring plural conditions, such as conditions within the body of a living subject.

A probe in accordance with one embodiment of the invention incorporates a light transmissive member, preferably a fiber optic. The probe also includes luminescent means connected to the light transmissive member in optical communication therewith, so that excitation light transmitted along the member will be applied to the luminescent means and such that response light emitted by the luminescent means will be transmitted back along the member. The luminescent means most preferably has plural emission modes with different lifetimes. Thus, the luminescent means is operative to emit a plurality of response light signals simultaneously into the light transmissive member in response to excitation light, each such response light signal representing one emission mode. Each different response light signal has a different decay time characteristics. The luminescent means is arranged to vary the lifetimes of different emission modes in response to different ones of the conditions to be monitored. For example, the luminescent means may be arranged to vary the lifetime of one emission mode, and hence the decay time of the corresponding response light signal, in accordance with changes in temperature, to vary another lifetime in accordance with changes in pH, another in accordance with changes in $CO_2$ concentration, and to vary another in accordance with changes in oxygen concentration.

The luminescent means may include a single luminescent material or else may include plural luminescent materials, each luminescent material having a different one of the emission lifetimes and each being sensitive to one or more of the conditions to be monitored. The luminescent means desirably are arranged to emit all of the response light signals in response to excitation light within a common band of excitation wavelengths applied through the light transmissive member. Also, the luminescent means may be operative to emit all of the response light signals within a common band of response light wavelengths. For example, all of the emission modes may be excited by a light at one excitation wavelength, and all of the response light signals may consist of emitted light at or about the same wavelength, or within relatively narrow, overlapping wavelength ranges.

It may be difficult or impossible to separate the response light signals from a probe in accordance with this aspect of the invention by optical filtering to segregate different wavelengths of response light. However, because the various emission modes have different lifetimes, information relating to each emission mode can be recovered and deconvoluted from information relating to other emission modes as further discussed below. To facilitate this recovery process, the ratio between the lifetime of each one of the emission modes of the luminescent means and the lifetime of each other one of such emission modes desirably is at least about 1.15:1, even higher ratios being more preferred. The need to provide different lifetimes normally does not seriously restrict the choice of available luminescent materials sensitive to various conditions. There is no need to restrict the choice of luminescent materials to allow wavelength-based signals separation, and no need for precise wavelength-restrictive optical filters.

A further aspect of the present invention provides apparatus for monitoring plural conditions. This apparatus may include a light transmissive member and luminescent means for emitting response light connected to such member in optical communication herewith, the luminescent means having plural emission modes with different lifetimes and being operative to vary each of the lifetimes in response to a condition to be monitored. The apparatus preferably further includes excitation light source means for simultaneously applying a plurality of excitation light components varying cyclically in amplitude at a plurality of modulation frequencies to the luminescent means through the light transmissive member. The luminescent means accordingly emits response light simultaneously incorporating a plurality of response light components, each varying cyclically in amplitude at one of the modulation frequencies. The response light components cooperatively represent a plurality of the emission modes of the luminescent means, preferably all of such modes.

The apparatus preferably further includes transducer means for deriving a multicomponent response signal, desirably an electrical signal, incorporating components at a plurality of these modulation frequencies from the response light so that the multicomponent response signal represents a plurality of the emission modes. More preferably, the apparatus also includes interpretation means for deriving information relating to each emission mode, such as the lifetime of each such emission mode or the contribution of such emission mode to the total luminescent emissions. The interpretation means thus recovers information relating to the lifetime or intensity of each emission mode.

The interpretation means desirably includes means for determining the phase and degree of modulation of each component, as by transforming a set of samples of the response signal into a frequency-domain representation of the signal. The interpretation means may be arranged to determine a phase difference for each modulation frequency, i.e. the difference in phase between the component of the response light at that modulation frequency and the corresponding component of the excitation light at the same modulation frequency. The apparatus may also be arranged to determine a modulation ratio for each modulation frequency, i.e. a ratio between the absolute modulation of the response light component at a particular modulation frequency and the absolute modulation of the excitation light component at the same modulation frequency. As further discussed below, the interpretation means desirably is arranged to derive at least one of $S^*\omega)$ and $G(\omega)$ for each said modulation frequency where:

$S(\omega) = M(\omega) \sin[\Delta\phi(\omega)]$ (1)

$G(\omega)\ 32\ M(\omega) \cos[\Delta\phi(\omega)]$ (2)

and where $\omega$ represents any one of said modulation frequencies, expressed as an angular frequency;

M(ω)

is the value of modulation ratio for such modulation frequency; and

Δφ(ω)

is said phase difference for such modulation frequency. Most preferably, the interpretation means is arranged to derive lifetimes of the various emission modes, or fractional contributions of each emission mode to the emission at each particular frequency by solving a plurality of simultaneous equations selected from the group consisting of equations of the form:

$$S(\omega) = \sum_{i=1}^{N} \frac{f_i \omega \tau_i}{1 + \omega^2 \tau_i^2}, \quad (3)$$

equations of the form:

$$G(\omega) = \sum_{i=1}^{N} \frac{f_i}{1 + \omega^2 \tau_i^2} \quad (4)$$

and combinations thereof, wherein: N represents an integer number of said emission modes; $f_i$ represents the contribution of response light arising from the $i^{th}$ said emission mode to the luminescence of frequency w as a fraction of the total amplitude of said response light at frequency w; and $\tau_i$ represents the lifetime of the $i^{th}$ emission mode.

Preferred apparatus in accordance with this aspect of the invention provides for deconvolution of information pertaining to each emission mode from information regarding the other emission modes using reasonable linearized data fitting algorithms such that the data fitting can be accomplished in real time while measurements are taken. This is of particular value in biomedical monitoring and similar applications. Most preferably, the data is collected by direct sampling of the response signal as discussed above in connection with the aforementioned '131 application. The excitation light source means desirably is arranged to provide the excitation light components as a plurality of sets, each such set including one or more components, and typically a plurality of components, within a selected range of modulation frequencies. The range of modulation frequencies of each such set is different from the range of modulation frequencies of every other one of the sets. Preferably, the excitation light source means is arranged to provide the excitation light such that each set includes a principal component having a principal period between about 20 and about 100 times the lifetime of one of the emission modes of luminescent means. Each such set preferably includes one or more additional components at modulation frequencies about 2 to about 32 times the modulation frequency of the principal component in such set. The additional components in each set may be harmonics of the principal component.

Most preferably, the interpretation means includes frequency separation means for separating the multicomponent response signal into a plurality of separated responses signals, each such separated response signal including only components within one such range of modulation frequencies, such as one fundamental and its harmonics. As further discussed below, such a separation can simplify the sampling and frequency-domain transformation processes.

Still further aspects of the invention provide methods of monitoring plural conditions. Such methods desirably include the steps of applying excitation light as discussed above to luminescent means via a light transmissive member as discussed above. The methods preferably further include the step of deriving the multicomponent response signal and derivation of information relating to each emission mode, as by derivation of phase angle and modulation values as discussed above, from that signal. Desirably, the step of deriving information includes the step of solving the simultaneous equations discussed above. The conditions to be monitored most preferably include conditions within the body of a living subject as, for example, chemical concentrations and temperatures within the body.

These and other objects, features and advantages of the present invention will be more readily apparent from the detailed description of the preferred embodiments set forth below, taken in conjunction with the accompanying drawings.

BRIEF DESCRIPTION OF THE DRAWINGS

FIG. 1 is a schematic, block diagram view of apparatus in accordance with one embodiment of the invention.

FIG. 2 is a fragmentary, diagrammatic sectional view, on an enlarged scale, of a portion of the apparatus shown in FIG. 1.

DETAILED DESCRIPTION OF THE PREFERRED EMBODIMENTS

Figure 3:
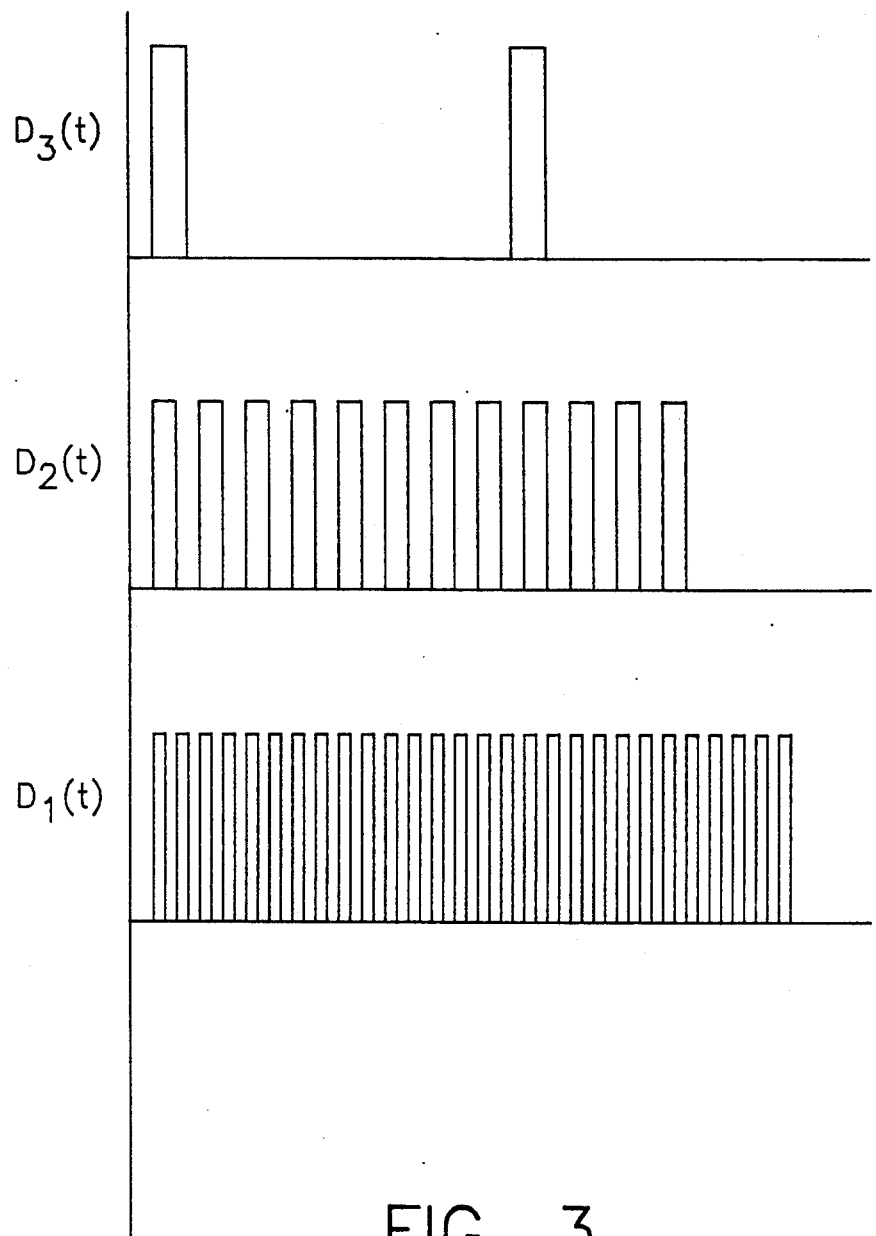
FIGS. 3 and 4 are idealized graphs of certain waveforms used in methods according to one embodiment of the invention.

Apparatus according to one embodiment of the invention includes a probe 100. Probe 100 includes an elongated optically transmissive fiber 102 having a proximal end 104 and a distal end 106. Fiber 102 is a graded or step index optical fiber. It includes a core 108 and a cladding 110 surrounding the core along the entire length of the fiber. Both the core and the cladding are formed from transparent materials such as quartz, but the cladding has a slightly lower refractive index than the core. The fiber 102 is generally circular in a cross section. Its outside diameter $d_o$ is less than about 450 micrometers preferably less than about 200 micrometers and most preferably less than about 140 micrometers. Its core diameter $d_c$ is about 60-80% of the outside diameter, viz, about 100 micrometers where the outside diameter is about 140 micrometers and typically less than about 100 microns.

A composite luminescent body 112 is mounted at the distal end 106 of the fiber. The diameter of body 112 (its dimension in the direction transverse to the direction of elongation of fiber 102) is substantially the same or only slightly larger than the outside diameter $d_o$ of fiber 102. Body 112 includes an oxygen-sensitive mass 114 of a luminescent composition comprising a phosphorescent material embedded in an oxygen-permeable transparent plastic resin. Desirably, mass 114 is bonded to the fiber by adhesion of the plastic resin 50 to the material of the fiber. The oxygen permeable plastic resin may be a polyurethane such as Pellethane sold by Dow Chemical or a silicone-polycarbonate resin such as that sold by General Electric Corporation. The phosphorescent material has a substantial sensitivity to oxygen, and desirably a substantial quenching of phosphorescence in the presence of oxygen. Among the materials which may be employed are the metallo derivatives of compounds selected from the group consisting of porphyrin; chlorin; bacteriochlorin; porphyrinogen; and the alkyl or aryl substituted derivatives of these compounds. All of the compounds have characteristic multi-ring structures with plural nitrogen atoms juxtaposed with one another adjacent the center of the structure. In the metallo derivatives, a metal atom or ion is disposed adjacent the center of the structure and is commonly considered as being bound to the nitrogen atoms of the multi-ring structure. Among the metallo derivatives which may be employed are those bearing metals selected from the group consisting of platinum and palladium. Combinations of these metals may also be used. A particularly preferred oxygen-sensitive luminescent material is platinum tetraphenyl porphyrin, commonly referred to as "platinum porphyrin".

The phosphorescent platinum porphyrin in mass 114 can absorb excitation light of about 400nm to about 550 nm wavelength, and can emit response or phosphorescent light at about 600 nm to about 750 nm. When isolated from oxygen, the phosphorescent material in mass 114 has phosphorescent decay lifetime of about 50 microseconds. This lifetime is reduced to about 15 microseconds under partial pressures of oxygen as commonly encountered during operation of the instrument.

The composite luminescent mass 112 further includes a pH sensitive mass 116. Mass 116 may include a luminescent material which is sensitive to pH but substantially insensitive to oxygen. The luminescent material may be incorporated in a water-permeable polymer such as a methacrylate or an acrylamide. As used in this disclosure, the term "luminescent material," includes a combination of materials which cooperate to give the desired luminescent properties and/or sensitivity to the condition to be monitored. As disclosed in Jordan et al, Physiological pH Fiber-optic Chemical Sensor Based on Energy Transfer, Anal. Chem. 1987 vol. 59, pp. 437-439, a pH sensitive luminescent material may include a fluorophore such as eosine and an absorber such as phenol red co-immobilized or bound in a methacrylamide polymer. In such a system, the fluorophore itself may be insensitive to the condition to be monitored such as pH but the absorber may absorb energy from the fluorophore, and thus diminish the net response or emission light, by directly absorbing response light emitted by the fluorophore or by non-radiative energy transfer from the fluorophore to the absorber so that the absorber serves to quench the fluorescence of the fluorophore. Both phenomenon may occur in the same luminescent composition. As the characteristics of the absorber change in response to changes in pH the degree of such absorption and/or quenching also changes, and hence the response of the luminescent material changes. Where the absorber provides quenching, the decay time characteristics of the response light will vary with the characteristics of the absorber.

The eosine/phenol red composition in mass 116 will absorb excitation light from about 400 nm to about 500 nm, and will emit response light at about 600 nm to about 750 nm. At the pH levels encountered in physiologic sensing, such as those within the blood, the lifetime of the emission will be about 0.1 microseconds.

A further mass 118 of a luminescent composition sensitive to carbon dioxide is also provided at the distal end 106 of the fiber optic. The carbon dioxide sensitive composition of mass 118 may incorporate a pH sensitive luminescent material and water permeable polymer similar to those employed in pH-sensitive mass 116, together with a bicarbonate and water buffer. Mass 118 may include a coating of a water impermeable, ion-permeable material to prevent drying of the buffer during storage. As the $CO_2$ concentration in the environment changes, the pH of the buffer changes as well, thus altering the emission lifetime of the luminescent material. The absorption and emission wavelengths of mass 118 are identical to those of mass 116. Within the range of $CO_2$ concentrations normally encountered in physiological systems, however, the pH of the buffer is outside the range of pH of the blood and hence the lifetime of emissions from mass 118 is 15 considerably less than that for mass 116. The emission lifetime of mass 118 typically is about 0.01 microsecond.

The probe additionally includes a temperature sensitive mass 120 including a ruby crystal. The ruby crystal absorbs excitation light between 300 and 670 nm, and emits response light at about 620 to about 760 nm. The emission lifetime varies with temperature, but is about 300 microseconds at physiologic temperatures.

The apparatus further includes a central control computer 20 having a memory 22 and data input and output device 24. The apparatus further includes a programmable crystal clock 26 arranged to provide clock pulses at a predetermined frequency. A programmable pulse generator 28 is arranged to provide rectangular wave pulses at three different fundamental excitation frequencies $F_{e1}$; $F_{e2}$ and $F_{e3}$ and at three different sampling frequencies $F_{s1}$; $F_{s2}$ and $F_{s3}$ determined by counting clock signals from clock 26. The pulse generator 28 is arranged so that the frequencies of the rectangular wave pulses can be selected by computer 20, as by adjusting the number of clock signals from clock 26 to be counted off by pulse generator 28 during each cycle. Further, the pulse generator is arranged to vary the breadth or duty cycle of the rectangular wave pulses as directed by computer 20.

Pulse generator 28 is connected to a superposition circuit 29 arranged to merge the separate pulse trains at the separate excitation frequencies $F_{e1}$; $F_{e2}$ and $F_{e3}$ into a single drive signal. The output of superposition circuit 29 is connected to a light pulse source 30.

The light pulse source includes an electrically controlled light emitting structure. This structure may be a device such as one or more light emitting diodes or a combination of elements such as a continuous wave laser coupled to an acousto-optic modulator or other device arranged to control passage of light responsive to applied electrical signals. The light source is arranged to emit light in a band of wavelengths encompassing the absorption wavelength ranges of all of masses 114, 116, 118 and 120. The light output of pulse source 30 is connected through a controlled variable aperture 32 to the input of a conventional optical switching and coupling apparatus 36. Switch and coupler 36 is connected to a measurement light path 38 into the proximal end 104 of the fiber optic in probe 102. Switch and coupler is also connected to a reference light path 40, which desirably has the same overall length as measurement light path 38, and which has a mirror or other reflecting surface at an end remote from the switch and coupler device. Switch and coupler 36 has an output connection 42 linked to a detector 56.

Detector 56 is arranged to convert light into electrical signals such that the amplitude of the electrical signals is directly related to the amplitude of the incoming light supplied to the detector. Desirably, the detector is a sensitive device having a very fast response time. Suitable detectors include photomultiplier tubes such as those supplied under the designation R928 by Hamamatsu Photonics K. K., Hamamatsu, Japan; and include avalanche photodiodes and microchannel plates, also available from the same supplier. The electrical output of detector 56 is connected to an amplifier 58. The output of amplifier 58 is connected to three signal processing channels 59a, 59b and 59c. Each channel 59 includes an electrical bandpass filter 60. The filters 60a, 60b and 60c of the different channels have different bandpass characteristics, as further discussed below. The output of each bandpass filter 60 is connected to the signal input of a triggerable analog to digital or "A/D" converter 62. Each converter 62 is arranged to capture the instantaneous amplitude of the electrical signal passed through the associated filter 60 upon receipt of a triggering signal, and to deliver the captured value in digital form. The output of each converter 62 is connected through a direct memory access device 64 to the memory 22 of the computer 20, so that digital values supplied by each converter 64 can be written into predetermined locations in memory 22 rapidly, without interrupting operation of the processor in computer 20. The trigger input of each converter 62 is connected to an output of pulse generator 28 carrying pulses at one sampling frequency $F_s$, so that each such pulse will trigger converter 62 to capture a further sample. Thus, converter 62a is connected to receive the first sampling frequency $F_{s1}$; converter 62b receives sampling frequency $F_{s2}$ and converter 62c receives sampling frequency $F_{s3}$.

The electrical output from amplifier 58 is also connected to a feedback aperture control circuit 65. Control circuit 65 is linked to computer 20 so that control circuit 65 can receive a target or set point value for the amplitude of the electrical signal from filter 60. Control circuit 65 is also linked to aperture 32, and aperture 32 is responsive to control signals from circuit 65. Thus, the aperture control circuit is arranged to adjust aperture 32 so as to maintain the peak amplitude of the signal from amplifier 58 at the selected set point. Aperture control circuit 65 is also arranged such that it will only adjust the aperture 32 upon appropriate command from computer 20 and, in the absence of such command, aperture control 65 will maintain the setting of aperture 32 at a constant value.

In a method according to one embodiment of the invention, probe 100 is inserted into a living subject so that the distal end 106 of the probe is disposed within the subject and hence exposed to conditions prevailing within the subject. As shown in FIG. 1, the distal end 106 of optical fiber 102 may be inserted into the blood vessel B of a living subject S, such as a human or other mammal via a conventional intravascular catheter such as an intravenous or intraarterial catheter 151. Because the fiber 102 and the masses 112-118 the luminescent composition at the distal end of the fiber are of relatively small diameter, such insertion may be performed readily. For example, catheter 151 may be a conventional 22 gauge catheter having an interior diameter of about 450 micrometers, and the fiber 102 may be threaded readily through such a catheter. The ability to use such a small catheter for insertion of the probe affords significant advantages in that such a small catheter is itself relatively easy to position within the blood vessel and causes only minimal trauma to the subject. The probe is positioned so that the distal end 106 lies within the blood vessel whereas the proximal end 104 of fiber 102 lies outside of the subject and hence is readily accessible for connection to switch and coupler 36. With the probe in position, the oxygen permeable plastic resin in mass 114 reaches equilibrium with the oxygen content of the blood in blood vessel B, so that the luminescent material within the mass is exposed to an oxygen concentration which varies with the oxygen concentration prevailing within the blood. Likewise, the water-permeable material of mass 116 attains the pH of the blood, whereas the $CO_2$-permeable material of mass 118 attains equilibrium with the $CO_2$ dissolved in the blood and mass 120 attains the temperature of the blood.

Computer 20 actuates the apparatus so as to perform a predetermined routine. The computer selects a set of three fundamental frequencies $F_{e1}$; $F_{e2}$ and $F_{e3}$ to be applied, based upon instructions provided to the computer via data input and output unit 24. Typically, the fundamental frequencies are directly selected by the operator from prior knowledge of the decay time range of the composition in the various masses. Thus, for each luminescent composition in masses 114-120 of the probe, at least one of the fundamental frequencies should be selected so that the repetition time $T_e$ between succeeding pulses at that frequency is longer than the decay time of the luminescence of the mass. Desirably, for each mass 114-120, the repetition period Te for one frequency Fe is about 20 times to about 100 times the expected decay time. For the preferred materials discussed above, having decay times of about 300, about 30, about 0.1 and about 0.01 microseconds, $F_{e1}$ should be about 1 MHz, Fe2 about 100 KHz and $F_{e3}$ about 1 KHz. The fundamental frequencies $F_{e1}$; $F_{e2}$ and $F_{e3}$ should not be integral multiplies of one another.

The computer sets clock 26 to generate clock pulses at a rate substantially higher than the fundamental frequencies $F_{e1}$; $F_{e2}$ and $F_{e3}$, and actuates pulse generator 28 to provide a separate drive signal D(t) as a series of electrical rectangular-wave pulses at each fundamental frequency $F_e$. As illustrated schematically in FIG. 3, drive signal $D_1(t)$ is at a relatively high frequency $F_{e1}$; drive signal $D_2(t)$ is at intermediate frequency $F_{e2}$ and drive signal $D_3(t)$ is at a low frequency $F_{e3}$. Superposition unit 29 provides a composite signal incorporating all of these drive signals together to light source 30, so that source 30 provides light varying in accordance with the composite drive signal.

Figure 4:
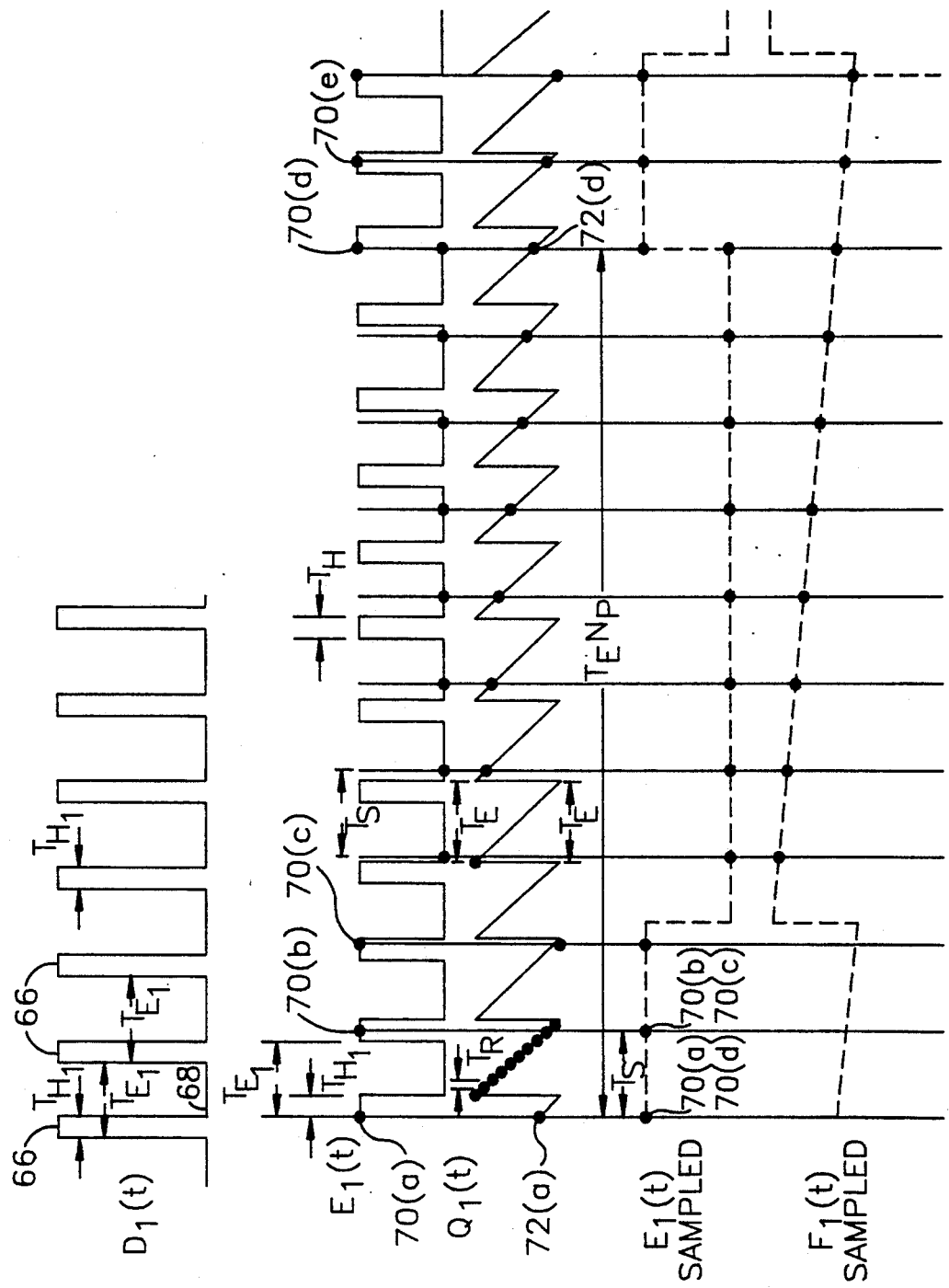

The computer also controls pulse generator 28 to control the duty cycle of each drive signal waveform. FIG. 4 depicts one drive signal $D_1(t)$. As indicated in FIG. 3, that drive signal $D_1(t)$ alternates between a high state 66 and a low state 68 on each cycle. The time $T_{h1}$ during which the waveform is on or high is a relatively small proportion of the total excitation cycle time $T_{ei}$. The fraction $T_{h1}/T_{e1}$, the proportion of high or on time during each cycle is referred to herein as the "duty cycle" of the waveform. As will be readily appreciated from standard principles of mathematics, such a rectangular waveform includes a fundamental component at $F_{e1}$ and harmonic components at frequencies which are multiples of $F_{ei}$. The other components $D_2(t)$ and $D_3(t)$ likewise have relatively small duty cycles, and likewise include harmonics of their respective fundamental frequencies.

The composite drive signal is applied to light source 30, thus activating the light source to emit excitation light varying repetitively in amplitude at each of the three fundamental excitation modulation frequencies $F_{e1}$; $F_{e2}$ and $F_{e3}$, and at harmonics of each such fundamental excitation modulation frequency.

The computer also actuates pulse generator 28 to produce a series of triggering pulses at three sampling frequencies $F_{s1}$; $F_{s2}$ and $F_{s3}$, having corresponding sampling periods $T_{s1}$, $T_{s2}$ and $T_{s3}$. The first sampling frequency $F_{s1}$ and sampling period $T_{s1}$ is associated with the high-frequency first fundamental excitation frequency $F_{e1}$ and excitation cycle time or period $T_{e1}$. Sampling frequency $F_{s1}$ is selected to provide coherent wave-skipping sampling as discussed below. Thus, the first sampling period $T_{s1}$ is selected such that $T_{s1}$ differs slightly from one excitation period time $T_{e1}$ of the associated excitation waveform, or from some integral multiple of that excitation $T_{e1}$. The preferred relationship between $T_{s1}$ and the associated $T_{e1}$ is:

$$T_s = T_e N_\omega + T_e/N_p \tag{5}$$

where $N_w$ is a positive integer which may be 1 or greater than 1 and $N_p$ is a rational number having an absolute value greater than 1. Most preferably, $N_p$ is an integer. $N_p$ may be positive or negative. Each of the other sampling frequencies $F_{s2}$ and $F_{s3}$, associated with the lower fundamental excitation frequencies may be similarly related to its associated fundamental excitation frequency, to provide a similar coherent wave-skipping sampling.

The modulated excitation light from source 30 passes through aperture 32, to switch and coupler 36. Computer 20 initally executes a reference cycle, during which it commands the switch and coupler to pass the excitation light into reference path 40, and to pass the reflected light from the reference path into detector 56. Detector 56 provides an electrical signal representing this excitation light impinging on the detector. Aperture control 65 detects the peak amplitude of the signal from amplifier 58 and adjusts the aperture 32 to bring the amplitude of this signal into a specified range, within the operating range of converters 62. Once this adjustment has been accomplished, the aperture control 65 maintains aperture 32 at a constant setting. Thus, $F_{s1}$ is a slightly lower frequency than $F_{e1}$. However, either or both of the sampling frequencies used with the lower-frequency excitation signals $F_{e2}$ and $F_{e3}$, respectively, may be higher than the associated fundamental excitation frequency.

The electrical signal from amplifier 58 during this stage of the method is a composite reference signal representing the excitation light applied by light pulse source 30 through optical components 32, 36 and 40, together with any amplitude changes, phase shift or distortion introduced by these components or by detector 56, and amplificater 58 itself. This composite electrical signal accordingly includes components at all of the fundamental excitation modulation frequencies $F_{e1}$; $F_{e2}$ and $F_{e3}$ and at harmonics of those frequencies.

The bandpass filter 60 of each channel 59 is arranged to pass signals in a preselected range corresponding to one of the fundamental excitation modulation frequencies and a reasonable set of harmonics of that fundamental. For example, filter 60c may have a passband of about 10 Hz to about 2,000 Hz; filter 60b may have a passband of about 10 KHz to about 1 MHz, and filter 60a may pass frequencies from about 5 MHz upward. The bandpass filters thus segregate the composite excitation signal into three separate partial excitation signals $E_1(t)$; $E_2(t)$ and $E_3(t)$ representing components at excitation modulation frequencies within separate ranges, and pass these separate excitation signals to separate sampling devices or A/D converters 62a, 62b and 62c, respectively.

Each partial excitation signal E(t) is substantially in the form of a rectangular wave having the same frequency $F_e$ and repetition period $T_e$ as one original driving signal D(t). For example, partial excitation signal $E_1(t)$ is shown in FIG. 23 with the corresponding drive signal $D_1(t)$. Each analog to digital converter 62 samples the partial excitation or reference electrical signal passing through filter 60. The reference electrical signal provided by the detector is sampled directly, i.e., without any intermediate cross-correlation, mixing, or frequency-shifting steps. Stated another way, each component of the signal reaching the sampling device or converter 62 includes the same frequencies as the corresponding component in the signal provided by detector 56.

Upon each pulse of the trigger or sampling signal $F_{s1}$ supplied by pulse generator 28, analog to digital converter 62a takes a sample by capturing the amplitude of the reference signal $E_1(t)$ at the instant of the trigger pulse and provides a digital word representing that amplitude. Memory access unit 64 accepts these digital words as the same are generated by analog to digital converter 62 and stores them in order in memory 22. This series of operations continues, so that a reference or excitation series of values is stored in memory 22. Because the repetition period $T_{s1}$ of the sampling or trigger signal applied to A/D converter 62 is slightly different than the repetition period $T_{e1}$ of the excitation signal, each sample captured by A/D converter 62 occurs at a slightly different point in the waveform of the partial excitation signal $E_1(t)$. In FIG. 3, the time of each sample is indicated on the $E_1(t)$ waveform as a black dot. The first such sample 70(a) occurs at the beginning of an "on" or high period. The next sample 70(b) occurs slightly after the beginning of the "on" period during the next cycle of $E_1(t)$. Sample 70(c) occurs at a slightly later point on the waveform and so on.

In the example depicted in FIG. 4, the sampling period $T_{s1}$ is just slightly more than one $T_{e1}$ of the excitation waveform $E1(t)$. That is, $N_w=1$ in the expression $T_s=N_w T_e/N_p$. Where $N_w$ is greater than one, entire periods of $E_1(t)$ without samples occur between successive samples. The difference between the time $T_s$ between successive samples and an integral multiple of the period $T_e$ of the excitation waveform is a rational fraction of $T_e$, i.e., $T_e/N_p$ with $N_p$ being a rational number. In the example shown in FIG. 4, $N_p$ is an integer having absolute value greater than one. Therefore, the $(N_p+1)$th sample falls on the same point of the $E_1(t)$ waveform as the first sample. Thus, sample 70(d) is taken at exactly the same point of the $E_1(t)$ waveform as sample 70(a). Stated another way, on each sample the sample is delayed relative to the $E_1(t)$ waveform by $T_e/N_p$, so that after $N_p$ samples have been taken, the accumulated delay of the sample relative to the waveform is equal to $T_e$, i.e., one full repetition period of the waveform, and hence the next sample falls on the same point of the waveform as the first sample. Thus, the sampling is coherent with the excitation waveform. Every $N_p$ samples constitute a complete representation of a single cycle of the waveform. The sampling is continued over a sufficient time to accumulate many times $N_p$ samples.

While the samples are being acquired, computer 20 averages together all of the samples taken from a given point in the waveform. Thus, the computer averages the value recorded at sampling point 70(a), the value recorded at sampling point 70(d) and the value recorded at other sampling points (not shown) at the same point in the waveform, so as to derive an averaged value for all of the samples at this point in the waveform. In like fashion, computer 20 computes an average for all of the samples representing the second point in the waveform, i.e., for sample point 70(b), sample 70(e) and other, similar values (not shown). Standard computer averaging techniques are used in this stage of the process. Thus, the individual samples are added into $N_p$ running totals maintained in $N_p$ separate memory registers. The computer directs every $(N_p+1)$th sample into the same memory register and the sample is added to the running total in that register. Each total is subsequently divided by the number of samples included in the total. $N_p$ separate averages are computed in this way. These $N_p$ averaged sample values constitute a sampled excitation signal, and collectively represent the complete waveform of the excitation signal $E_1(t)$. Although the sampling period $T_{s1}$ is actually longer than the repetition period $T_{e1}$ of the waveform, the effective sampling rate is multiplied by a factor approximately equal to the absolute value of $N_wN_p$. Because the waveform is represented by $N_p$ sampled points, the effect is substantially the same as if the sampling rate were about $N_wN_p$ times as great, or as if the fundamental frequency of the excitation waveform $E_1(t)$ were divided by about $N_wN_p$. This effect is indicated by the hypothetical $E_1(t)$ sampled waveform depicted in broken lines in FIG. 3. Thus, the interval $T_s$ between successive samples is only a small fraction of the multiplied repetition period of the broken line waveform.

This effect can be explained in terms of sampling theory. Conventional and well-known sampling theory states that with ordinary, non wave-skipping sampling at a sampling rate $F_s$, the samples provide complete information as to the phase and modulation of components in the waveform up to a maximum frequency $F_h$ where $F_h=F_s/2$. With conventional sampling of a waveform having fundamental frequency $F_e$, $F_s=N_pF_e$ where $N_p$ is the number of samples per cycle of the waveform. Thus, for ordinary non wave-skipping sampling, $F_h=N_pF_e/2$. The same relationship between $F_h$, $N_p$ and $F_e$ applies to wave-skipping sampling. However, with wave-skipping sampling as described above, the relationship between $F_s$ and $F_e$ is different. For coherent wave-skipping sampling: $F_s=N_pF_e/(_wN_p+1)$. Thus, the relationship between the highest frequency for which information is provided by the samples and the sampling frequency is: $F_h=(N_wN_p+1)F_s/2$. Stated another way, wave-skipping sampling multiplies the maximum frequency $F_h$ observable with a given sampling rate $F_s$ by a factor of about $N_wN_p$.

Conventional, readily available sampling and digitizing equipment such as conventional sample-and-hold circuits and analog to digital converters provide a maximum sampling frequency $F_s$ up to about 20 MHz. However, the value of $N_wN_p$ may be up to about several hundred or more. Thus, even with conventional sampling equipment, maximum values of $F_h$ up to several GHz can be obtained using the wave-skipping sampling technique. Specialized high rate sampling and digitizing equipment can provide even greater $F_s$ and correspondingly greater $F_h$ using the wave-skipping technique.

Although sampling devices are ordinarily regarded as taking a point sample along a waveform, a real sampling device such as a sample-and-hold circuit actually provides a sample signal representing a portion of the waveform during some small but nonetheless finite sample capture interval. The wave-skipping technique does not appreciably enlarge the allowable sample capture interval. The sample capture interval used in wave-skipping sampling should be no more than the sample capture interval used with ordinary sampling, and desirably should be less than $T_e/N_p$.

The partial excitation signals $E_2(t)$ and $E_3(t)$ are sampled and digitized by A/D converters 62b and 62c, respectively, using sampling $F_{s2}$ and $F_{s3}$. Because partial excitation signal $E_3(t)$ includes only low-frequency components, the wave-skipping sampling technique is unnecessary. Thus, because the highest component in $E_3(t)$ is at 2000 Hz, a sampling frequency $F_s3$ will within the capabilities of conventional A/D 20 converters, say about 10 KHz, will provide adequate conventional sampling. Likewise, conventional sampling can be used for the mid-range signal as a sampling frequency of about 10 MHZ would be workable. The samples representing $E_2(t)$ and $E_3(t)$ are averaged over plural cycles in the conventional manner. Thus, each partial excitation signal is separately sampled and averaged.

To minimize aliasing, the harmonic content of each partial excitation signal, $E_3(t)$, desirably is limited to frequencies of about $F_h$ and below, by selecting the duty cycle of the associated partial excitation waveform $D(t)$ such that the duty cycle $T_h/T_e$ is less than $1/N_p$.

After a predetermined number of samples have been taken with respect to the excitation waveforms, computer 20 actuates optical switch 36 to direct the excitation light into the probe 100, thus starting a test cycle. During the test cycle, the excitation light is directed into the proximal end 104 of optical fiber 102 and passes through the optical fiber to the masses 114, 116, 118 and 120 of luminescent composition. While the repetitively varying excitation light is applied to the luminescent compositions, each composition emits light in response to each pulse of excitation light, and the intensity of each pulse of emitted light decays after the end of each pulse of excitation light. Stated another way, masses 114, 116, 118 and 120 emit response light varying repetitively at response modulation frequencies corresponding to the various excitation modulation frequencies. The response light thus will have components varying in amplitude at fundamental response modulation frequencies equal to the fundamental excitation frequencies, and at harmonics thereof. The repetitively varying emitted or response light is directed through the optical fiber 102 to the proximal and thereof and through switch 36 into detector 56. The emitted or response light impinging on detector 56 is converted by the detector and by amplification circuit 58 into a composite electrical response signal. At the beginning of the test cycle, aperture control unit 65 adjusts the aperture 32 so that the response light emitted by the luminescent compositions in the probe will produce an electrical signal from amplifier 58 of the appropriate magnitude.

The composite electrical response signal, incorporating components at all of the aforementioned response frequencies, is passed to bandpass filters 60a, 60b and 60c, which segregate it into separate parts or partial response signals $Q_1(t)$, $Q_2(t)$ and $Q_3(t)$ in the same ranges as discussed above with reference to the excitation signal. Thus, the filters segregate the composite response signal into separate parts or partial response signals, each including one fundamental response signal and a reasonable number of harmonics thereof.

The partial response signal $Q_1(t)$ passing to converter 62a from bandpass fitler 60a is depicted schematically as in FIG. 4. The response signal $Q_1(t)$ has the same fundamental frequency $F_{e1}$ and the same repetition period $T_{e1}$ as the corresponding excitation signal $E_1(t)$. Analog to digital coverter 62a is operated in the same way as discussed above with reference to the excitation signal to take a series of samples of the response signal $F_1(t)$, using the same sampling frequency $F_{s1}$ and sampling period $T_{s1}$. Here again, the sampling rate is coherent with the fundamental frequency of the waveform, in that the time $T_{s1}$ between samples differs from the nearest integral multiple of the fundamental period $T_{e1}$ of the waveform by a small amount $T_e/N_p$ where $N_p$ is a rational number having an absolute value greater than one. Therefore, after a finite number of fundamental periods or cycles of the waveform, the sample is taken at the same point of the $Q_1(t)$ waveform as previously taken. Again, $N_p$ is an integer, so that after $N_p$ samples have been taken, the sampling point falls at the same point in the waveform as previously sampled. Thus, as indicated in FIG. 4, the sampling point 72(b) falls at the same point on the $Q_1(t)$ waveform as sampling point 72(a), taken $N_p$ samples previously. Here again, the effect is substantially the same as if the sampling rate were about $N_wN_p$ times higher or as if the frequency of the sampled $Q_1(t)$ were about $N_wN_p$ times lower, as indicated by the waveform $Q_1(t)$ sampled in FIG. 4. The same increase in maximum observable frequency $F_h$ discussed above with reference to the excitation waveforms also applies in sampling of high-frequency partial response signal $Q_1(t)$. The lower frequency partial-response signal $Q_3(t)$ and mid-frequency range partial response signal $Q_2(t)$ are sampled using conventional sampling techniques. As with the excitation samples, the response samples for each partial response signal are captured and stored by memory access unit 64 in memory 22 in sequence, and plural samples representing the same point on the partial response waveform are averaged by computer 20 to provide an average value for each sampled point on the waveform.

The computer applies a standard, well-known digital fast Fourier transform algorithm separately to the data for representing each partial excitation signal $E_1(t)$, $E_2(t)$ and $E_3(t)$ and each partial response signal $Q_1(t)$ and $Q_2(t)$, $Q_3(t)$ separately. Thus, the data for each such partial signal is separately transformed into a Fourier series expansion. The Fourier series expansion $(FS)_{Q1(t)}$ of the partial response signal $Q_1(t)$ is given by the expression:

$$(FS)_{Q1(t)} = \sum_{n=1}^{n=N_2/2} R_{n,r}\cos(2\pi nF_{e1}t) + I_{n,r}\sin(2\pi 1nF_{e1}t) \quad (6)$$

where: $R_{n,r}$ is the real magnitude of the response signal component of the $n^{th}$ harmonic of the first fundamental frequency $F_{ei}$ and $I_{n,r}$ is the imaginary magnitude of the response component at the $n^{th}$ harmonic. The Fourier 20 series expansion $(FS)_{E1(t)}$ of the sampled partial excitation signal $E_1(t)$ is given by an expression of the same format incorporating coefficients $R_{n,e}$ and $I_{n,e}$ representing the real and imaginary magnitudes, respectively, of the excitation signal component at the $n^{th}$ harmonic of the same frequency.

In the same manner, the computer obtains the Fourier series expansions of the second partial excitation signal $E_2(t)$ and second partial response signal $Q_2(t)$, and the expansions of the third partial excitation signal $E_3(t)$ and third partial response signal $Q_3(t)$. The computer thus obtains values for I and R for each of various harmonic and fundamental frequencies in each of the partial excitation and partial response components. For convenience, each such frequency F may be expressed as an angular frequency $$\omega$$

where $$\omega = 2\pi F \quad (7)$$

For each such angular frequency, the phase delay or difference in phase between the response component at a given frequency and the excitation component at the same frequency is given by the expression:

$$\Delta\phi(\omega) = \arctan\left(\frac{I_{\omega,E}}{R_{\omega,E}}\right) - \arctan\left(\frac{I_{\omega,R}}{R_{\omega,R}}\right) \quad (8)$$

In this expression, the subscripts E and R denote excitation and response, respectively, whereas the subscript omega denotes the angular frequency in question. The absolute modulation for any given angular frequency in a given partial response signal is given by $$M_{\omega,R} = \frac{\sqrt{(R_{\omega,R}^2 + I_{\omega,R}^2)}}{R_{0,R}} \quad (9)$$

where $R_{O,R}$ is the average intensity of the particular partial response signal. Likewise, the absolute modulation of each component in a given partial excitation signal is given by $$M_{\omega,E} = \frac{\sqrt{(R_{\omega,E}^2 + I_{\omega,E}^2)}}{R_{0,E}} \quad (10)$$

In which $R_{O,E}$ is the average intensity of the partial excitation signal. Using these absolute modulation values, a modulation ratio for each angular frequency is given by:

$$M(\omega) = \frac{M_{\omega,R}}{M_{\omega,E}} \quad (11)$$

As pointed out above, the response-light sent to detector 56 from probe 100 includes light from all luminescent material masses 114, 116, 118 and 120. The composite response signal from detector 56 likewise represents light from all of the masses. In the general case, each component of the response signal at each frequency arises in part from light emitted by each of the four luminescent materials. Thus, in general, each response component at each frequency incorporates information about all of the four decay modes of the four luminescent materials. Thus, the phase difference $$\Delta\phi(\omega)$$

calculated by the formula set forth above for any single frequency depends in part upon the luminescent decay time of each of the four emission modes. Likewise, the modulation ratio $$M(\omega)$$

for a given frequency would also be a function of all of the various decay times. Moreover, in the general case the modulation ratio and phase difference also depend upon the fractional contribution $f_i$ of each luminescent decay mode to the total luminescence. The fractional contribution $f_1$ of the $i^{th}$ decay mode as used in this disclosure refers to the percentage of photons in the total response light contributed by emission in that particular mode. The effect of the fractional contributions on phase differences and modulation ratios for the various frequencies on the fraction contributions of the various decay modes can be understood qualitatively. If a particular decay mode contributes most of the photons, the response light as a whole would tend to have properties resembling light which would be emitted by a single luminescent substance having only that decay mode. If a different decay mode becomes relatively brighter and thus has a higher fractional contribution, the properties of the light, including phase difference at any particular frequency and modulation ratio at any particular frequency would shift to better resemble the properties of the newly brightened decay mode.

To recover useful information about the conditions to be monitored, it is necessary to segregate information about each individual decay mode. For example, either the lifetime or the fractional contribution of decay mode 114 alone must be recovered in order to determine the oxygen concentration of the blood in blood vessel B, and either the fractional contribution of the decay mode of mass 116 or the decay lifetime of that individual decay mode must be recovered in order to ascertain the pH of the blood and so on.

To permit such segregation or deconvolution of that concerning the individual decay modes from the composite, conjoined data, computer 20 calculates one or both of $$S(\omega)$$

and $$G(\omega)$$

for each modulation frequency where $$S(\omega) = M(\omega)\sin[\Delta\phi(\omega)] \quad (1)$$

and $$G(\omega) = M(\omega)\cos[\Delta\phi(\omega)] \quad (2)$$

After calculation of parameters S and G, the computer uses these calculated values in a plurality of simultaneous equations which may include equations of the form $$S(\omega) = \sum_{i=1}^{N} \frac{f_i \omega \tau_i}{1 + \omega^2 \tau_i^2} \quad (3)$$

equations of the form $$G(\omega) = \sum_{i=1}^{N} \frac{f_i}{1 + \omega^2 \tau_i^2} \quad (4)$$

or both in combination. In these equations, i is an index variable representing the $i^{th}$ emission mode; n is an integer number of emission modes and $$\tau_i$$

is the decay lifetime of the $i^{th}$ emission mode.

These equations incorporate the underlying assumption that each decay mode is a simple exponential decay. Given that assumption, however, these formulas permit ready and simple deconvolution of the data about the various decay modes. Thus, where there are a given number of decay modes, there are 2N-1 unknowns. Provided that data for at least N modulation frequencies is available, parameters S and G will be available for 2N equations, so that the problems reduces to a set of simultaneous equations with the same number of equations as unknowns. Reasonable computer algorithms for solving sets of simultaneous equations with as many equations as unknowns are wellknown in the computation arts and need not be described herein. Where more than N modulation frequencies are employed, as with the three fundamentals and plural harmonics of each fundamental discussed above, various sets of 2N equations may give slightly different results. The computer selects values for the unknowns which give the lowest total error when substituted into all of the equations. Thus, the computer can calculate values of fractional contributions and lifetimes using various sets of 2N equations and average the various values for each such fractional contribution and each such lifetime obtained from the various sets of equations. In effect, this incorporates data from more than N modulation frequencies and hence results in a solution which effectively averages the data obtained at the various modulation frequencies.

The calculations can be simplified even further by using known values for some of the unknowns. In particular, the fractional contributions $f_i$ typically vary over only a relatively small range during operation of any given instrument with a given subject. Accordingly, the computer may calculate values of $f_i$ and lifetimes using 2N simultaneous equations for N emission modes as discussed above and then, after values of $f_i$ have been determined the computer may treat these values as known constant values during subsequent operations. Thus, after determining $f_i$, the computer may continue to calculate new values for each emission mode lifetime during continued operations based upon the assumption that all values of $f_i$ remained constant. Such subsequent calculations require only N simultaneous equations for N emission modes. Alternatively, values of the fractional contributions of the various emission modes under reasonable ranges of conditions (such as those encountered in physiologic situations)

may be determined or specified by the probe manufacturer in advance.

Where such known or assumed values of the fractional contributions $f_i$ are employed, fewer simultaneous equations must be solved to arrive at values of lifetimes for the various emission modes. Accordingly, the simultaneous equations can be solved more quickly. In this case, only a minimum of N simultaneous equations are required with N emission modes. However, more than N simultaneous equations may be employed in this case to permit use of data from more than N modulation frequencies with the averaging effect discussed above.

Moreover, the slow-decaying components do not contribute appreciably to light modulated at frequencies far shorter than the reciprocal of their respective decay times. Said another way, for those modulation frequencies where $$\omega \gg \frac{1}{\tau_i}$$

for the $i_{th}$ decay mode, the terms corresponding to the ith decay mode in the simultaneous equation discussed above may be considered 0. Conversely, for very low modulation frequencies, such that $$\omega \ll \frac{1}{\tau_i}$$

for the $i_{th}$ decay mode, the terms representing the $i^{th}$ decay mode in equation (3) above for parameter S may be considered as equal to 0, whereas each term for the $i^{th}$ decay in equation (4) for parameter G may be considered as equal to 1. Expressed qualitatively, this indicates that fast decay time luminescence contributes response light which is effectively in phase with the excitation light at low frequencies and hence has 0 phase shift. Equations simplified in this manner have fewer unknowns so that their solution becomes even simpler. In the embodiment discussed above, if the probe 100 is selected so that all of the luminescent contributions of the individual decay modes are equal, the aforementioned simultaneous equations reduce to:

$$S(\omega) = 0.25 \left( \frac{\omega\tau_1}{1 + \omega^2\tau_1^2} + \frac{\omega\tau_2}{1 + \omega^2\tau_2^2} + 0 \right) \quad (12)$$

and $$G(\omega) = 0.25 \left( \frac{1}{1 + \omega^2\tau_1^2} + \frac{1}{1 + \omega^2\tau_2^2} + 2 \right) \quad (13)$$

for modulation frequencies in the low range, passed-by filter 60c. For modulation frequencies in the high range, passed by filter 60a, the equations reduce to $$S(\omega) = 0.25 \left( \frac{\omega\tau_3}{1 + \omega^2\tau_3^2} + \frac{\omega\tau_4}{1 + \omega^2\tau_4^2} + 0 \right) \quad (14)$$

and $$G(\omega) = 0.25 \left( \frac{1}{1 + \omega^2\tau_3^2} + \frac{1}{1 + \omega^2\tau_4^2} + 0 \right) \quad (15)$$

Thus, in a rapid estimation mode, the computer may calculate two values of S, two values of G for each of two frequencies in the low range or, a value of S and a value of G for one frequency in the low range and then solve two simultaneous equations to obtain decay times for the longest lived decay modes. The computer may likewise calculate values of S for two different frequencies in the high range, values of G for two different frequencies in the high range or a value of S and a value of G for one such frequency in the high range and then obtain values of the decay times of the shortest lived decay modes. The computer may alternate such rapid estimations with calibration cycles using the full sets of simultaneous equations discussed above. During rapid estimations, the computer may disable the intermediate channel 59b, as by disabling analog-to-digital converter 62b and by actuating pulse generator 28 so that the intermediate frequency of pulse train $F_{e2}$ is omitted. This reduces the amount of data collected and thus permits the computer to perform the rapid estimations more frequently. Thus, the computing capacity of computer 20 may be selected such that the calculations required for full data collection and full solution of all of the simultaneous equations can only be performed relatively infrequently, as required during calibration, whereas the smaller number of computations required for the rapid estimation may be performed at reasonably close intervals during operation, so as to trap rapidly changing conditions within the subject.

As will be readily appreciated, numerous variations and combinations of the features discussed above can be utilized without departing from the present invention as defined by the claims. Merely by way of example, it is not essential that the various modulation frequencies be generated as plural fundamentals and harmonics thereof. other arrangements for generating multiple frequencies can be employed. Also, the deconvolution steps discussed above for recovering data relating to individual decay modes from a composite signal can be applied to a composite signal which has been frequency shifted using a cross-correlation signal. Thus, where the multi-component response and excitation signals are derived by a cross-correlation process, the components in the response and excitation signal will be at frequencies different from the modulation frequencies themselves, but nonetheless directly related thereto. Thus, each component in the response signal will represent a frequency-shifted transform of the response light at one modulation frequency. In this arrangement, as well as in the other arrangements discussed above, each component in the response signal is at a frequency corresponding to one modulation frequency. This is normally less preferred, however, because of the loss of signal to noise ratio at the higher harmonics which occurs in typical cross-correlation schemes.

In a further variant, the internal reflectance of the probe is treated as a further decay mode having 0 decay time. The simultaneous equations discussed above can be used to solve for the fractional contribution of this additional decay mode as well as for the decay modes attributable to luminescence. This allows the instrument to compensate for changes in internal reflectance. As these and other variations and combinations of the features discussed above can be utilized without departing from the present invention, the foregoing description of the preferred embodiments should be understood as illustrating rather than as limiting the present invention.

What is claimed is:

1. A probe for monitoring a plurality of conditions comprising:
   (a) a light-transmissive member for applying excitation light within a common band of excitation wavelengths;
   (b) luminescent means connected to said member in optical communication therewith, said luminescent means having a plurality of emission modes with different lifetimes, said luminescent means being operative to simultaneously emit a plurality of response light signals having wavelengths within a common band of response wavelengths into said light-transmissive member in response to the excitation light within the common band of excitation wavelengths applied through said light-transmissive member, each such response light signal representing one said emission mode, said luminescent means being operative to vary each of said lifetimes in response to one of said conditions to be monitored.

2. A probe as claimed in claim 1 wherein said light-transmissive member is an elongated fiber optic having proximal and distal ends.

3. A probe as claimed in claim 2 wherein said elongated fiber optic includes only a single fiber.

4. A probe as claimed in claim 2 wherein said luminescent means includes a plurality of luminescent compositions mounted to said distal end of said single fiber optic.

5. A probe as claimed in claim 1 wherein said luminescent means includes a plurality of luminescent compositions mounted to said light-transmissive member.

6. A probe as claimed in claim 1 wherein said luminescent means is operative to emit a plurality of said response light signals at a single common wavelength in response to substantially monochromatic excitation light.

7. A probe as claimed in claim 1 wherein said ratio between the lifetime of each one of said emission modes and the lifetime of each other one of said emission modes is at least about 1.15:1.

8. Apparatus for monitoring a plurality of conditions comprising
   (a) a light-transmissive member;
   (b) luminescent means for emitting response light connected to said member in optical communication therewith, said luminescent means having a plurality of emission modes with different lifetimes, said luminescent means being operative to vary each of said lifetimes in response to one of said conditions to be monitored;
   (c) excitation light source means for simultaneously applying a plurality of excitation light components varying cyclically in amplitude at a plurality of modulation frequencies to said luminescent means through said light transmissive member so that said luminescent means emits response light simultaneously incorporating a plurality of response light components each varying cyclically in amplitude at one of said modulation frequencies and so that said response light components cooperatively represent all of said plurality of emission modes of said luminescent means;
   (d) transducer means for deriving a multicomponent response signal incorporating components corresponding to a plurality of said modulation frequencies from said response light so that said multicomponent response signal represents a plurality of said emission modes; and
   (e) interpretation means for deriving information relating to each said emission mode represented by said multicomponent response signal from said multicomponent response signal.

9. Apparatus as claimed in claim 8 wherein said luminescent means includes a plurality of luminescent substances having different emission modes.

10. Apparatus as claimed in claim 8 wherein each ratio of one said lifetime to another one of said lifetimes is at least about 1.15:1.

11. Apparatus as claimed in claim 8 wherein said excitation light source means includes means for providing said excitation light components as a plurality of sets each including one or more of said components within a selected range of excitation modulation frequencies, the range of excitation modulation frequencies of each said set being different from the range of such frequencies of every other one of said sets.

12. Apparatus as claimed in claim 11 wherein said excitation light source means includes means for providing said excitation light components so that each said set includes a different principal excitation modulation frequency and so that each said principal excitation modulation frequency corresponds to a principal period between about 2 and about 100 times the lifetime of one of said emission modes.

13. Apparatus as claimed in claim 12 wherein said excitation light source means includes means for providing said excitation light components such that each said set includes a principal component at one of said principal excitation modulation frequencies and one or more additional components at excitation modulation frequencies about 2 to about 32 times the principal excitation modulation frequency in such set.

14. Apparatus as claimed in claim 13 wherein said interpretation means includes frequency separation means for separating said multicomponent response signal into a plurality of separated response signals, each said separated response signal including only components within one of said ranges of modulation frequencies.

15. Apparatus as claimed in claim 8 wherein said transducer means is also operative to derive an excitation signal representing said excitation light and incorporating components at said excitation modulation frequencies, said interpretation means including means for determining a phase difference for each said modulation frequency between the component of said response signal at such modulation frequency and the component of said excitation signal at the same frequency.

16. Apparatus as claimed in claim 15 wherein said interpretation means includes means for determining a modulation ratio for each said modulation frequency from said multicomponent response signal and said excitation signal.

17. Apparatus as claimed in claim 16 wherein said interpretation means includes means for deriving at least one of $S(\omega)$ $G(\omega)$ for each said modulation frequency where:

$$S(\omega) = M(\omega) \sin[\Delta\phi(\omega)] \qquad (1)$$

$$G(\omega) = M(\omega) \cos[\Delta\phi(\omega)] \qquad (2)$$

and where $\omega$ represents any one of said modulation frequencies, expressed as an angular frequency $M(\omega)$ is the value of modulation ratio for such modulation frequency; and $\Delta\phi(\omega)$ is said phase difference for such modulation frequency.

18. Apparatus as claimed in claim 17 wherein said interpretation means includes means for deriving lifetimes for said emission modes by solving a plurality of simultaneous equations selected from the group consisting of equations of the form:

$$S(\omega) = \sum_{i=1}^{N} \frac{f_i \omega \tau_i}{1 + \omega^2 \tau_i^2}, \qquad (3)$$

equations of the form:

$$G(\omega) = \sum_{i=1}^{N} \frac{f_i}{1 + \omega^2 \tau_i^2} \qquad (4)$$

and combinations thereof, wherein: N represents an integer number of said emissions modes; $f_i$ represents the contribution of response light arising from the $i^{th}$ said emission mode to the luminescence of frequency w as a fraction of the total amplitude of said response light at frequency w; and $\tau_i$ represents the lifetime of the $i^{th}$ emission mode.

19. Apparatus as claimed in claim 18 wherein said means for deriving lifetime for sad emission modes by solving a plurality of simultaneous equations includes means for solving said equations using known values for $f_i$ in each said equation.

20. Apparatus as claimed in claim 19 wherein said means for deriving lifetimes for said emission modes by solving a plurality of simultaneous equations includes means for deriving values for N said lifetimes by solving at least N said equations for at least N said modulation frequencies.

21. Apparatus as claimed in claim 18 wherein said means for deriving lifetimes for said emission modes by solving a plurality of simultaneous equations includes means for determining values for $f_i$ in said equations by solving said equations, said means for solving said equations being operative to derive values for N said lifetimes by solving at least 2N said equations for at leas N said modulation frequencies.

* * * * *